United States Patent
Gordon et al.

(10) Patent No.: US 8,800,554 B2
(45) Date of Patent: Aug. 12, 2014

(54) DRY POWDER INHALER

(75) Inventors: James Gordon, Nottingham (GB); Andrew Paul Morris, Nottingham (GB); Philip Carl Parkes, Nottingham (GB); Robert Andrew Rudge, Nottingham (GB); Douglas Robert Saunders Bradshaw, Royston (GB); John Philip Briant, Royston (GB); Adrian John Streeter, Royston (GB)

(73) Assignee: Innovata Biomed Limited, Edinburgh (GB)

( * ) Notice: Subject to any disclaimer, the term of this patent is extended or adjusted under 35 U.S.C. 154(b) by 325 days.

(21) Appl. No.: 12/812,582

(22) PCT Filed: Jan. 12, 2009

(86) PCT No.: PCT/GB2009/000074
§ 371 (c)(1),
(2), (4) Date: Jul. 12, 2010

(87) PCT Pub. No.: WO2009/087404
PCT Pub. Date: Jul. 16, 2009

(65) Prior Publication Data
US 2010/0288277 A1 Nov. 18, 2010

(30) Foreign Application Priority Data
Jan. 11, 2008 (GB) .................................. 0800457.4

(51) Int. Cl.
*A61M 15/00* (2006.01)
*A61M 16/00* (2006.01)
*B05D 7/14* (2006.01)
*B65D 41/00* (2006.01)
*B65D 53/00* (2006.01)
*B65D 83/06* (2006.01)

(52) U.S. Cl.
USPC ........................ 128/203.15; 215/45; 215/341

(58) Field of Classification Search
USPC ............. 128/203.12, 203.15, 203.19, 203.21, 128/203.23, 200.14–200.23; 604/68–72; 215/321, DIG. 3, 43, 45, 316, 341, 346; D24/110, 110.5; 220/304, 796, 220/801–804; 222/36, 325, 402.2
See application file for complete search history.

(56) References Cited

U.S. PATENT DOCUMENTS 6,176,238 B1    1/2001  McDerment
6,220,243 B1 *  4/2001  Schaeffer et al. ........ 128/203.15

(Continued)

FOREIGN PATENT DOCUMENTS

EP      1 300 171 A2    4/2003
WO      9013328 A1      11/1990

OTHER PUBLICATIONS

ISA210 PCT International Search Report for PCT/GB2009/000074 filed Jan. 12, 2009.
International Search Report and Written Opinion for International Application No. PCT/GB2009/000074 (mailed Jun. 5, 2009).

(Continued)

*Primary Examiner* — Tan-Uyen T Ho
*Assistant Examiner* — Mark K Han
(74) *Attorney, Agent, or Firm* — LeClairRyan, a Professional Corporation (57) ABSTRACT

A dry powder inhaler comprises at least one medicament reservoir and a closure member engaged with the reservoir so as to close an opening therein. A surface of the reservoir adjacent the opening and a surface of the closure member are in abutment, either directly or via a seal member interposed between the reservoir and the closure member. At least one abutting surface is formed with a projection that increases the contact pressure between said surfaces, thereby improving the seal between them and reducing the potential for ingress of moisture between said surfaces into the reservoir.

14 Claims, 9 Drawing Sheets

(56) References Cited

U.S. PATENT DOCUMENTS

| | | | |
|---|---|---|---|
| 6,810,873 | B1 | 11/2004 | Haikarainen et al. |
| 7,540,282 | B2 * | 6/2009 | O'Leary ................. 128/200.23 |
| 2003/0116157 | A1 | 6/2003 | Braithwaite et al. |
| 2003/0136405 | A1 | 7/2003 | Goede et al. |
| 2005/0098529 | A1 * | 5/2005 | Bloom et al. ................. 215/276 |
| 2007/0215152 | A1 | 9/2007 | Goede et al. |
| 2007/0246044 | A1 | 10/2007 | Peng et al. |
| 2009/0050149 | A1 | 2/2009 | Von Schuckmann et al. |

OTHER PUBLICATIONS

International Search Report and Written Opinion for International Application No. PCT/GB2009/000077 (mailed Apr. 3, 2009).

Celanese, "Focus on Efficiency and Increasing Value," London, 23 pages (Sep. 2002).

Miller et al., "Intelligent Products Enhance Patients' Quality of Life," Ticona, Reprinted from IAPD Magazine, Jun./Jul. 2002, 2 pages.

Ticona, "Ticona at Med Tech 2006," Press Release, 17 pages (2006).

* cited by examiner

DRY POWDER INHALER

This invention concerns improvements in or relating to inhalers, and in particular to improvements in dry powder inhalers, that is to say devices for the administration of powdered medicament by inhalation, and especially to improvements that reduce the susceptibility of such devices to moisture ingress.

The administration of medicaments by inhalation is well-known. A wide variety of medicaments are now administered by that route, for the treatment of a range of respiratory disorders.

Examples of medicaments used for the treatment of respiratory disorders include, among others, anti-allergic agents, eg cromoglycate, ketotifen and nedocromil; anti-inflammatory steroids, eg beclomethasone dipropionate, fluticasone, budesonide, flunisolide, ciclesonide, triamcinolone acetonide and mometasone furoate; bronchodilators such as $\beta_2$-agonists, eg fenoterol, formoterol, pirbuterol, reproterol, salbutamol, salmeterol, indacaterol and terbutaline, non-selective $\beta$-stimulants, eg isoprenaline, and xanthine bronchodilators, eg theophylline, aminophylline and choline theophyllinate; anti-muscarinics, eg trospium chloride and glycopyrrolate (racemate and enantiomers thereof); PDE4 inhibitors, eg cilomilast and roflumilast; calcium channel blockers, eg diltiazem, verapamil, amlodipine, felodipine, lercanidipine and nimodipine; and anticholinergic agents, eg ipratropium bromide, oxitropium bromide and tiotropium.

The most common form in which such medicaments are formulated for administration by inhalation is as a powder. In the past, many such compositions were formulated as pressurised aerosols, in which the powder medicament was suspended in a liquefied propellant. Due to the adverse environmental effects of the propellants conventionally used, however, there is now increased interest in the use of so-called dry powder inhalers (DPIs). In a DPI, a unit dose of medicament powder, either packaged as such or metered from a bulk reservoir of medicament, is presented to an airway and is then entrained in an airflow passing through the airway. The airflow is most commonly generated by the patient's act of inhalation.

For the effective treatment of conditions of the respiratory tract it is generally desirable that as high a proportion of the powder as possible should be in the form of particles that are sufficiently fine that they are able to penetrate deep into the airways, and in particular that they should be transported deep into the lung. An important parameter in assessing the effectiveness of powdered medicament intended for inhalation is therefore the fine particle fraction (FPF), which defines the fraction of the emitted dose from an inhaler that has the potential to be deposited in the lung. This fraction is often defined as the proportion of the medicament that is in the form of particles with a diameter of less than 5 µm.

The FPF will depend to some extent on the manner in which the medicament is formulated, but also is strongly dependent on the performance of the device (inhaler) from which the formulation is delivered. It is well known that one problem that can affect the performance of a dry powder inhaler is the ingress of moisture into the device, and in particular into the parts of the inhaler in which medicament is stored prior to delivery to a user of the inhaler. Such problems are particularly acute when the medicament is hygroscopic and/or when the inhaler is stored or used in climatic conditions that give rise to high humidity. Ingress of moisture into dry powder inhalers is therefore generally undesirable as it may lead to agglomeration of the powdered medicament, resulting in reduction of FPF, and potentially to clogging of the device and/or inaccurate dosing of the medicament. Furthermore, some medicaments are susceptible to chemical degradation in the presence of moisture.

There is therefore an ongoing requirement to improve the resistance of inhaler devices to the ingress of moisture.

There have now been devised improvements to dry powder inhalers that result in reduced ingress of moisture into the inhaler, and which may hence improve the performance of the inhaler.

Thus, according to a first aspect of the invention there is provided a dry powder inhaler comprising at least one medicament reservoir with an opening and a closure member engaged with the reservoir so as to close the opening, a surface of the reservoir adjacent the opening and a surface of the closure member being in abutment, either directly or via a seal member interposed between the reservoir and the closure member, wherein at least one abutting surface is formed with a projection that increases the contact pressure between said surfaces, thereby improving the seal between them and reducing the potential for ingress of moisture between said surfaces into the reservoir.

Preferably, the projection engages a deformable seal member provided on the underside of the closure member. Alternatively, a seal member may be interposed between the surface of the reservoir adjacent the opening and the closure member. The seal member may take the form of a ring, of similar shape to the projection, or the seal member may extend across substantially all of the underside of the closure member.

Most preferably, the seal member is formed integrally with the closure member, eg in a two-shot moulding process. The material of the seal member is most preferably an elastomer, and more preferably a thermoplastic elastomer. Particularly preferred materials include thermoplastic polyester elastomers, eg that sold under the trade name RITEFLEX® by Ticona UK Ltd of Stafford Court, Telford TF3 3DD, United Kingdom.

The projection preferably extends around the full circumference of the opening in the reservoir.

By "a projection that increases the contact pressure between said surfaces" is meant a projection that reduces the contact area between the surfaces, relative to the contact area that would exist (eg between two substantially planar surfaces) if the projection were absent. It is believed that the reduced contact area leads to an increase in the contact pressure between the closure member and the reservoir.

The projection preferably has a pointed profile, most preferably a substantially triangular profile.

The projection is most preferably provided at the periphery of the opening in the reservoir, and engages with a deformable seal provided on the underside of the closure member. Alternatively, the projection may be provided on the underside of the closure member, and may engage a deformable seal provided around the periphery of the opening in the reservoir. In further alternatives, the projection may be formed in the deformable seal member.

The closure member may take the form of a cap that engages with the reservoir in such a manner that the opening in the reservoir is closed off. Most conveniently, the cap engages the reservoir with a clip fitting, the cap and the reservoir being provided with cooperating formations that engage to bring about sealing engagement of the cap with the reservoir. For instance, the cap may be provided with deformable limbs that engage with suitable detents on the reservoir. The contact pressure between the cap and the reservoir may be adjusted by appropriate design of the cooperating formations.

The applicant has found that the sealing engagement of the closure member with the reservoir may also be improved by measures that increase the rigidity of the closure member, and which thereby reduce any tendency of the closure member to flex.

Thus, according to a second aspect of the invention, there is provided a dry powder inhaler comprising at least one medicament reservoir with an opening and a closure member engaged with the reservoir so as to close the opening, wherein the closure member is provided with one or more integral stiffening ribs.

It is found that by incorporating one or more stiffening ribs into the closure member, the degree of flexure of the closure member during normal use is reduced and this is found to improve the quality of the seal between the closure member and the reservoir. The ingress of moisture into the reservoir is thereby inhibited.

The components of dry powder inhalers according to the invention may be manufactured by conventional techniques. Most commonly, the components will be formed in plastics materials, by injection moulding processes.

Dry powder inhalers in which the inventive measures described herein may be particularly appropriate include those that comprise a medicament reservoir and a metering member that closes an opening in the reservoir and which is adapted to transfer a unit dose of medicament from the reservoir to a position from which the dose of medicament can be inhaled by the user of the device. Examples of such devices are those referred to by the names DUOHALER® and CLICKHALER®. The principle of operation of such devices is described in WO-A-92/00771 and WO-A-01/39823. The device includes a medicament reservoir (or more than one such reservoir), the lower end of which is closed by a rotatable metering member that is formed with a series of cups that are sized such that they can hold a unit dose of the medicament. Rotation of the metering member moves a cup from a first position in which it fills with medicament to a second position, external to the reservoir, at which the cup is positioned adjacent to the path of an airflow through the device, by means of which the dose can be entrained in the airflow and inhaled. In the DUOHALER® and CLICKHALER®, the metering members take the form of frustoconical members that are urged into close engagement with the lower part of the respective reservoirs. In other devices, the metering members may take other forms, eg members that move in a linear or reciprocating manner.

The inhaler according to the invention may be used to deliver any of a wide range of medicaments. Such medicaments include those that are suitable for the treatment of asthma, COPD and respiratory infections. Examples of such medicaments are given on page 1 hereof. Other classes of medicaments with which the inhaler may be used include the following:

antivirals, eg zanamivir, ribavirin, flumist, ruprintrivir and pleconaril; antibiotics, eg tobramycin, doripenem, pentamidine, promixin, aztreonam; and antifungals, eg amphotericin B (further examples of medicaments that may potentially be administered using inhalers according to the invention are given in Respiratory Care 2000; 45(7): 836-845);

immunogens for the prevention or treatment of meningococcal disease, meningitis, septicaemia, meningoccaemia, pneumonia, meningococci of any of groups A, B, C, Y, W135, X and/or Z, anthrax, plague, small pox, tularaemia, meliodosis, Q fever, botulism, typhus, cholera, yellow fever, brucellosis, encephalitis, ricin, salmonella, staphylococcal Enterotoxin B, human immunodeficiency virus, hepatitis B, cytomegalovirus, tuberculosis, and combinations thereof;

proteinaceous compounds, macromolecules, hormones, mediators, insulin, human growth hormone, leuprolide, alpha-interferon, growth factors, anticoagulants, immunomodulators, cytokines, nucleic acids and combinations thereof;

antimigraine compounds, particularly triptans. Preferably, the triptan comprises almotriptan, rizatriptan, naratriptan, zolmitriptan, sumatritpan, eletriptan, frovatriptan, and combinations thereof.

Inhalers according to the invention may also be used to deliver combinations of two or more different medicaments. Specific combinations of medicaments which may be mentioned include combinations of steroids and $\beta_2$-agonists. Examples of such combinations are beclomethasone and formoterol; beclomethasone and salmeterol; fluticasone and formoterol; fluticasone and salmeterol; budesonide and formoterol; budesonide and salmeterol; flunisolide and formoterol; flunisolide and salmeterol; ciclesonide and salmeterol; ciclesonide and formoterol; mometasone and salmeterol; and mometasone and formoterol. Another preferred combination is indacaterol and glycopyrrolate. Triple combinations include glycopyrrolate, salmeterol and mometasone; glycopyrrolate, indacaterol and mometasone; glycopyrrolate, salmeterol and ciclesonide; glycopyrrolate, indacaterol and ciclesonide. Some or all of the constituents of such combinations can be co-formulated and stored in a single medicament reservoir, but more preferably the individual medicaments that make up the combination are stored in separate reservoirs within the inhaler.

The invention will now be described in greater detail, by way of illustration only, with reference to the accompanying drawings, in which.

Figure 1:
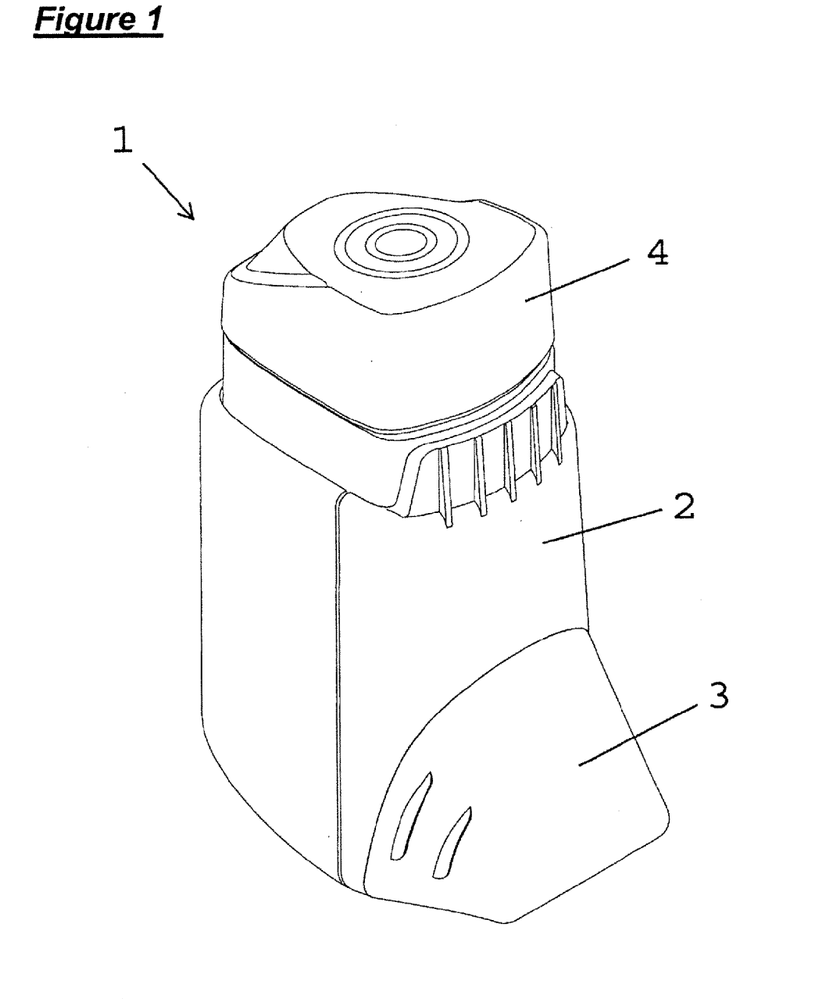
FIG. 1 is a perspective view of a dry powder inhaler according to the invention.

Referring first to FIG. 1, a dry powder inhaler of generally known form is designated 1 and is of the type known by the name DUOHALER®. The principle of action of such an inhaler is described in WO-A-01/39823 and in WO-A-2005/102429.

Essentially, the inhaler 1 comprises an inhaler body 2 with a mouthpiece that is covered by a removable shroud 3. The upper part of the inhaler 1 can be depressed relative to the inhaler body 2, the upper part thus constituting a push button 4 by means of which doses of medicament powders stored in bulk reservoirs within the inhaler body 2 can be dispensed from those reservoirs and inhaled by a user of the inhaler 1. Thus, in use, the user removes the shroud 3 to expose the mouthpiece, depresses the push button 4 to dispense unit doses of the medicaments, places the mouthpiece to his lips and inhales. The doses of medicament that have been dispensed from the bulk reservoirs are entrained in a flow of air through the inhaler 1 and are hence drawn into the user's lungs.

Figure 2:
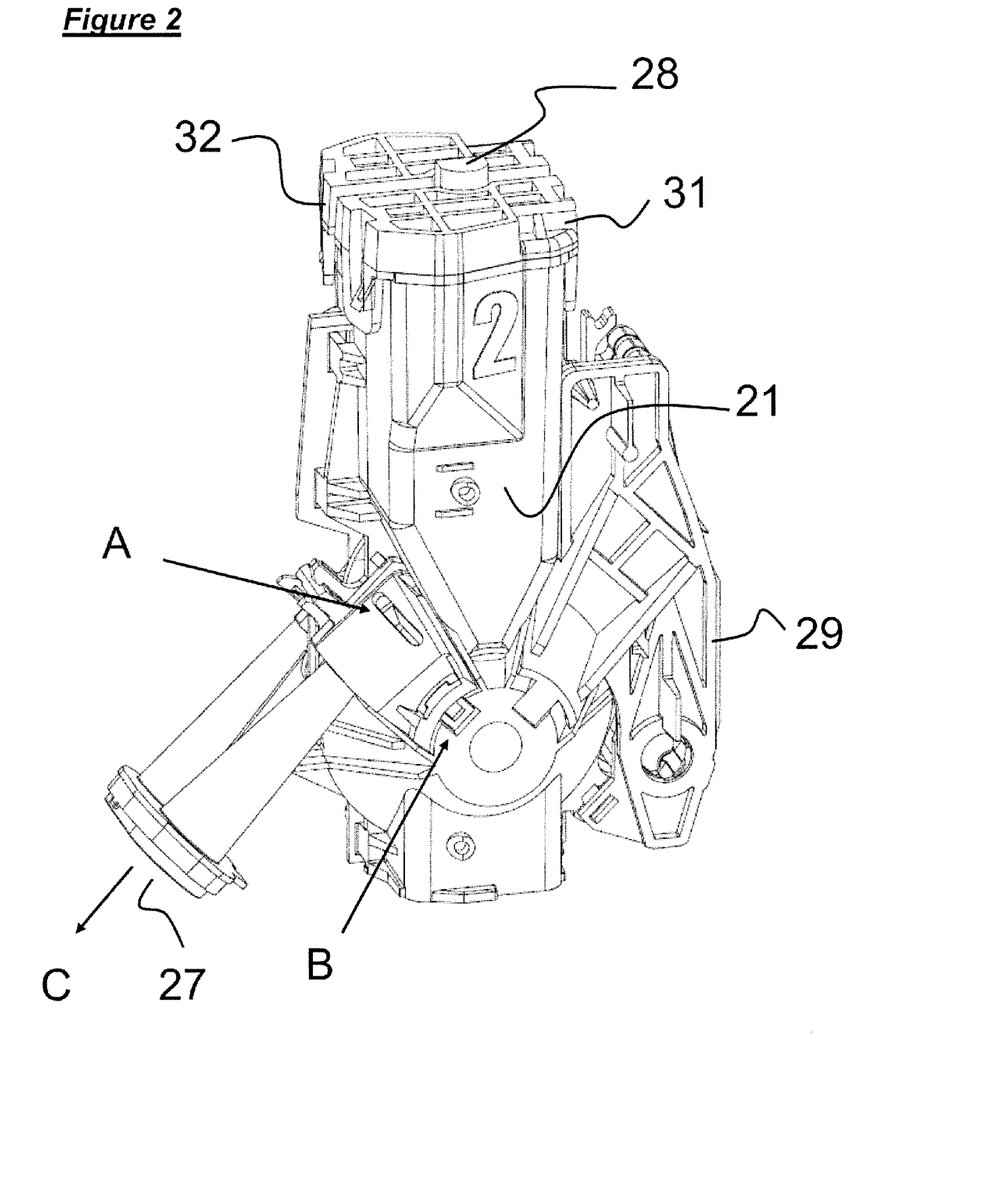
FIG. 2 is a perspective view of the internal components of the inhaler of FIG. 1.
Figure 3:
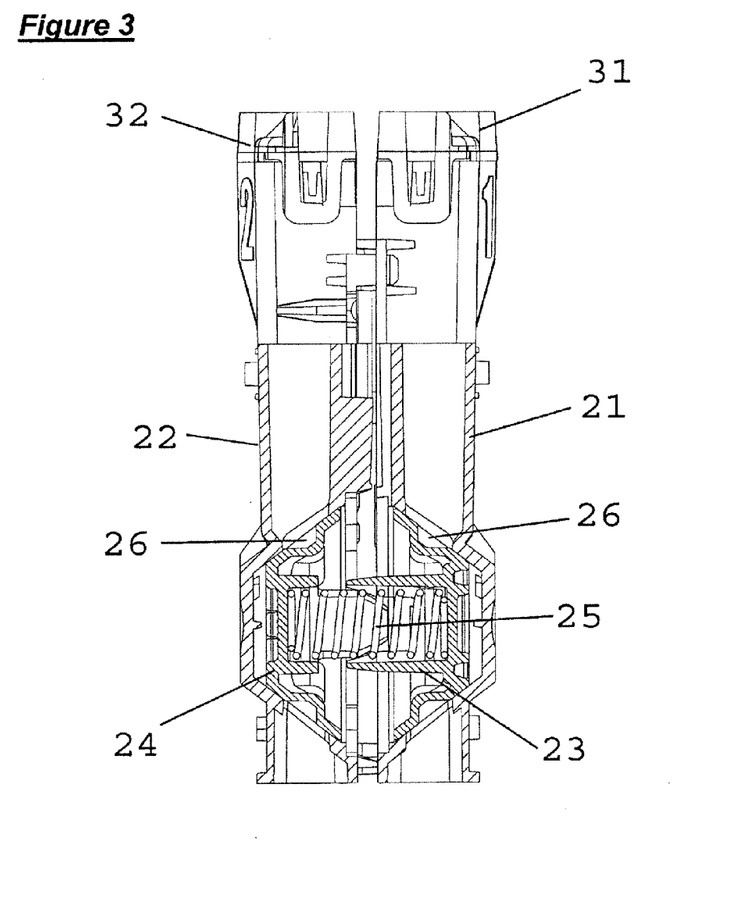
FIG. 3 is a side view, partly in section and partly cut away, of a pair of medicament reservoirs and associated dispensing mechanisms that form part of the inhaler of FIG. 1.

FIGS. 2 and 3 show the internal components of the inhaler 1 in greater detail. Specifically, the inhaler 1 comprises a pair of medicament reservoirs 21,22 that are arranged side-by-side. The lower end of each reservoir 21,22 is closed by a respective frustoconical metering member 23,24. The metering members 23,24 are mounted for rotation about a common axis that is transverse to the longitudinal axis of the reservoirs 21,22. Each metering member 23,24 is urged outwardly, into sealing engagement with its associated reservoir 21,22 by a compression spring 25.

Each metering member is formed with a series of cup-like depressions 26 in its surface, which depressions 26 serve for the volumetric metering of doses of medicament from each reservoir 21,22. In essence, the metering members 23,24 can be rotated in such a way that a depression 26 in each is brought into a filling position in which it is in registration with the bottom end of the associated reservoir 21,22, so that the depression 26 fills with a quantity of the medicament powder contained within that reservoir 21,22. Continued rotation then brings the filled depression into a dispensing position from which the dose of medicament can be entrained in an airflow (indicated by the arrows A, B and C in FIG. 2) passing over the depression 26, the airflow being caused by the user inhaling through the mouthpiece. The airflow, in which the medicaments are entrained, passes through an airway 27 that is housed within the mouthpiece. When the depression 26 is moved from the filling to the dispensing position, the next depression 26 is brought into registration with the bottom end of the reservoir 21,22, ie into the filling position.

The abutting walls of the reservoirs 21,22 are formed with hemi-cylindrical channels that together form a cylindrical channel within which an actuator 28 is slidably mounted. The upper ends of reservoirs 21,22 are closed by respective caps 31,32.

The actuator 28 is acted upon by the push button 4 and serves to index the metering members 23,24 such that a depression 26 in each is moved from the filling to the dispensing position. A counter unit 29 is attached to the rear of the reservoirs 21,22 and provides a visual display of the number of actuations of the inhaler 1 at a window (not visible in FIG. 1) in the rear of the inhaler body 2.

The manner in which the actuator 28 causes the metering members 23,24 to index and the manner in which the counter unit 29 records the number of actuations, as well as the details of the airway 27, are not pertinent to the present invention and will not be described in any greater detail.

The inhaler 1, as thus far described, is of known form. Specifically, the inhaler 1 is of the form known as DUO-HALER®, that has been developed by the present applicant, and which is a development of the inhaler sold under the name CLICKHALER®, a multi-unit-dose reservoir device marketed for the delivery of several different medicaments in Europe and Japan. Such an inhaler allows the independent containment and delivery of two dry powder formulations simultaneously.

Whilst the performance of the known inhaler is good, the applicant has sought to develop the device further, and in particular has developed refinements to the device that improve the performance of the device by reducing the ingress of moisture into the reservoirs 21,22. This improved performance, in particular resistance to moisture ingress, may be of importance for the delivery of active ingredients that are especially sensitive to moisture, and may thus extend the utility of the inhaler to the delivery of such medicaments.

In the inhaler of the present invention, modifications have been made, relative to the known form of inhaler, that improve the quality of the seal between the medicament reservoirs and their associated caps.

Figure 4:
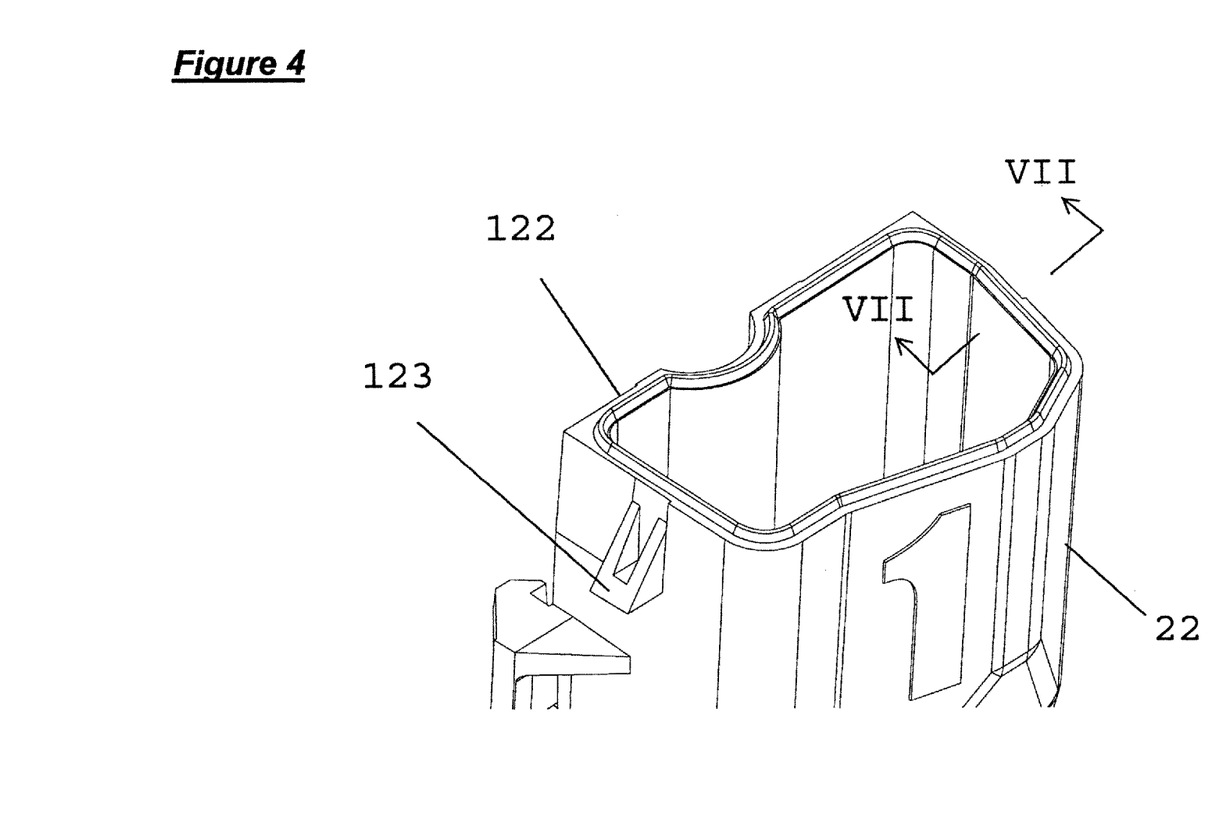
FIG. 4 is a perspective view of the upper part of a medicament reservoir forming part of the inhaler according to the invention.
Figure 7:
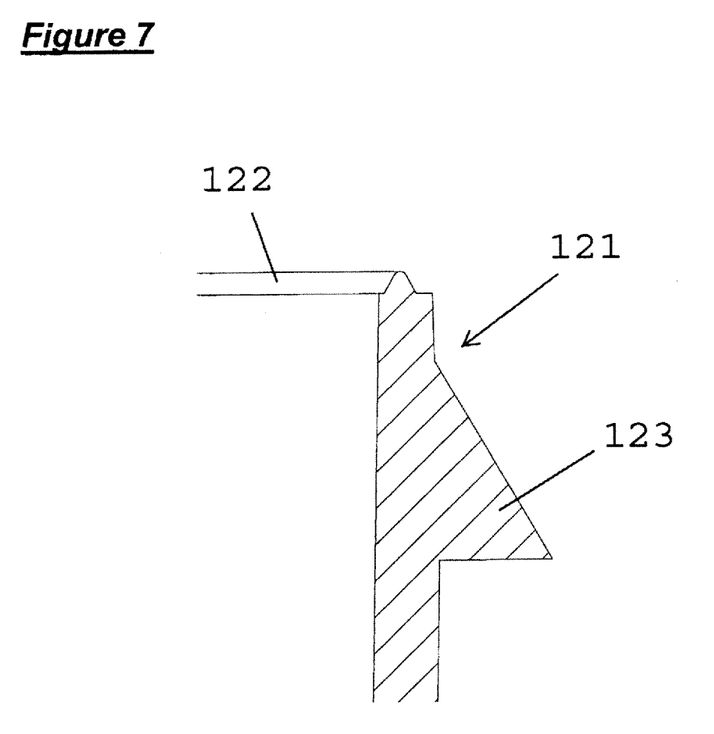
FIG. 7 is a cross-section on the line VII-VII in FIG. 4.

Referring now to FIG. 4, there is shown the upper part of the medicament reservoir 22. It can be seen that the rim of the reservoir 22 is formed with an upstanding ridge 122. The ridge 122 is of generally triangular cross-section (see FIG. 7).

Figure 5:
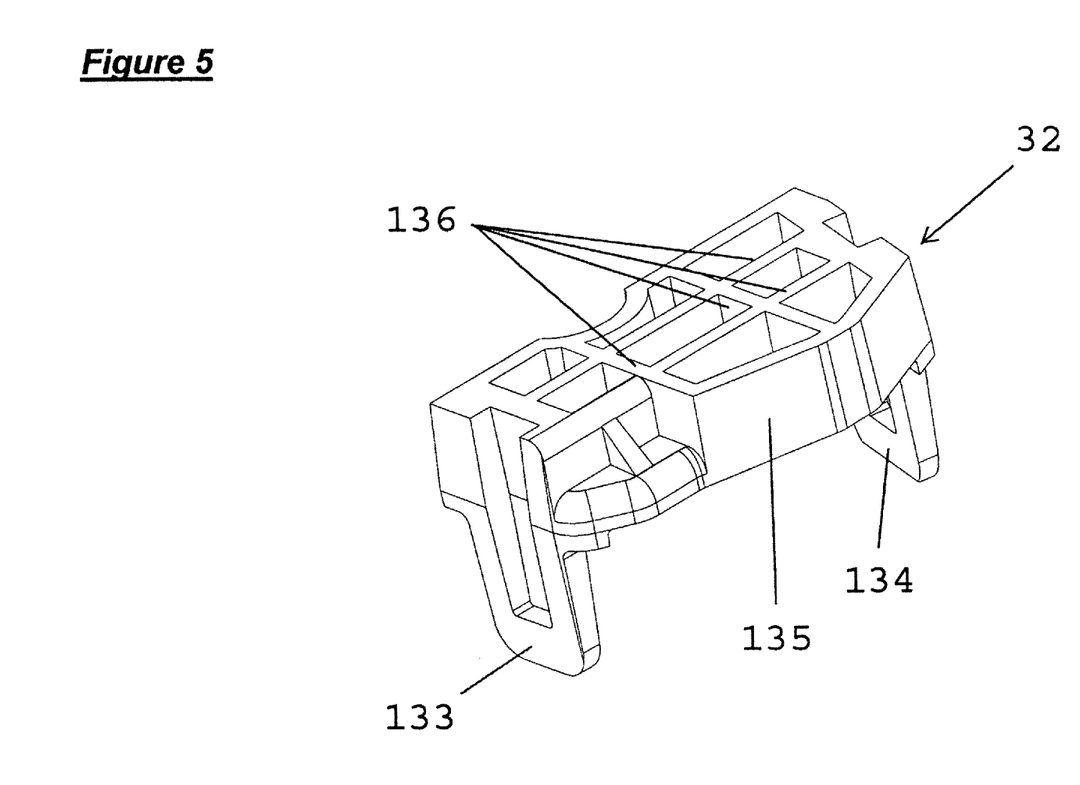
FIG. 5 is a perspective view of a medicament reservoir closure cap that forms part of the inhaler according to the invention.
Figure 6:
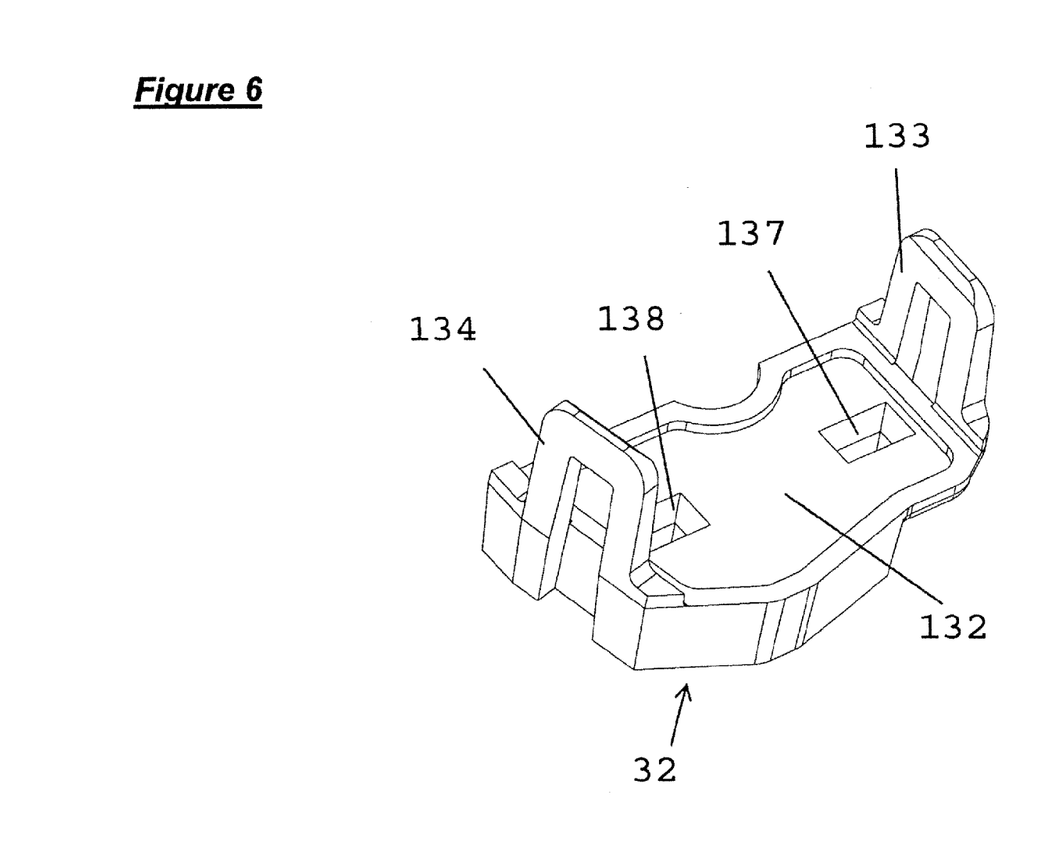
FIG. 6 is a perspective view of the cap of FIG. 5 in an inverted condition.

FIGS. 5 and 6 show the modified form of cap 32 that is used in the inhaler according to the invention. The cap 32 comprises a planar base 132 from opposite ends of which depend a pair of clips 133,134 that engage cooperating detents 123 on the external surface of the reservoir 22 (one of the detents 123 being visible in FIG. 4). A wall 135 extends upwardly from the base 132 around the full periphery of the cap 32, and stiffening ribs 136 extend across the cap 32, connecting opposite parts of the wall 135. The effect of the wall 135 and ribs 136 is to increase the stiffness of the cap 32. As can be seen in FIG. 6, in the embodiment illustrated, the base 132 of the cap 32 is slightly recessed and has a pair of slots 137,138 located close to the clips 133,134. A seal 141 of thermoplastic elastomer is formed in the second stage of a two-shot moulding process, and occupies the recess in the underside of the cap 32 and the slots 137,138. In other embodiments, the ribs 136 are partially reduced in height, so that the thermoplastic elastomer is able to flow, in the moulding process, through the slots 137,138 and to meet and form a bar extending across the upper side of the cap 32, thereby captivating the seal 141 on the cap 32. In yet further embodiments, the recess in the base 132 and the slots 137,138 are omitted, the seal 141 simply being formed on the planar underside of the base 132. The seal 141 is not shown in FIG. 6, but can be seen in FIG. 8.

Figure 9:
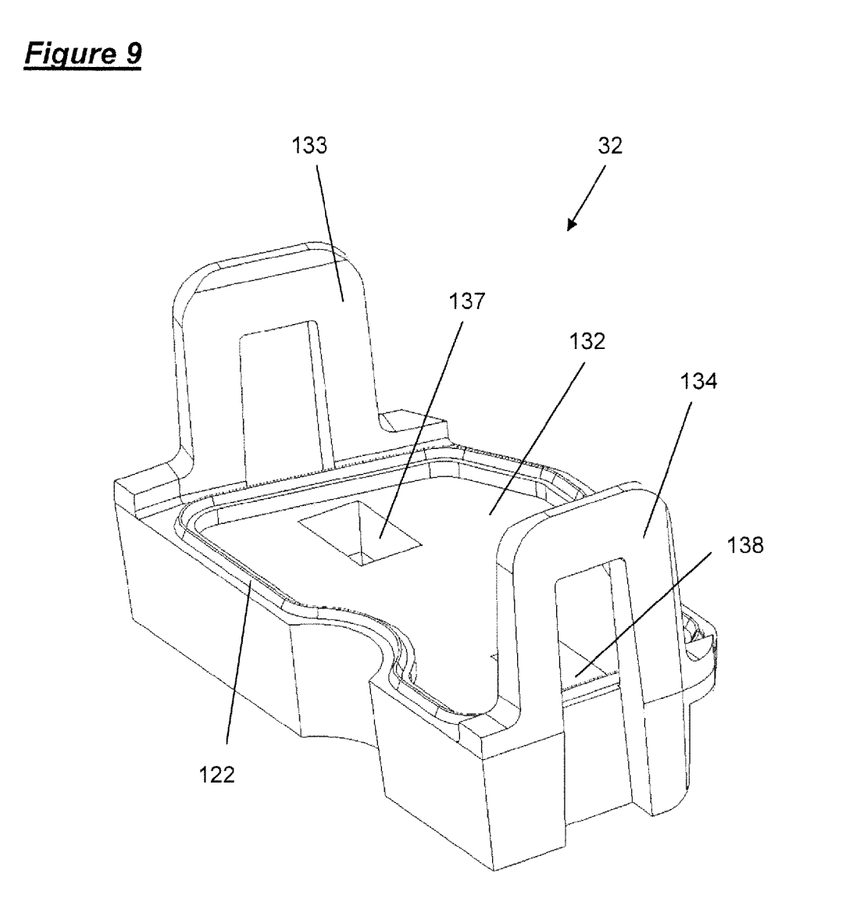
FIG. 9 is a perspective view of an embodiment of a medicament reservoir closure cap that forms part of the inhaler according to the present invention; the cap is an inverted condition.

FIG. 9 shows an embodiment of the cap 32 used in the inhaler according to the present invention. As shown in FIG. 9, the ridge 122 may be provided on the underside of the cap 32 around the periphery of the recess in the base 132 and may engage the seal 141.

Figure 8:
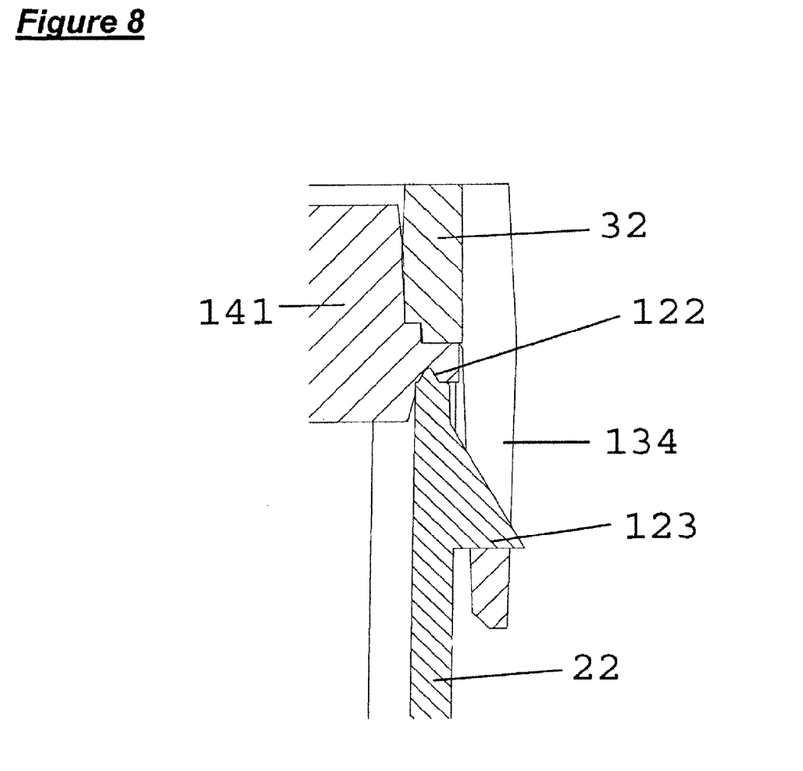
FIG. 8 is a view similar to FIG. 7, but showing the same region of the medicament reservoir when the cap of FIG. 5 is engaged therewith.

The cap 32 is engaged with the reservoir 22 as shown in FIG. 8. The cap 32 is clipped onto the top of the reservoir 22 such that the clips 133,134 engage the detents 123. The upstanding ridge 122 engages and deforms the seal 141, the form of the ridge 122 increasing the contact pressure between the ridge 122 and the seal 141, and thereby reducing the potential for ingress of moisture into the reservoir 22 between the upper edge of the reservoir 121 and the cap 32.

The cap 31 that is engaged with the reservoir 21 is identical in form to the cap 32, save that it is the mirror image of that cap 32.

It will be appreciated that, in addition to the features of the present invention, further measures may be taken to reduce the extent of moisture ingress into the inhaler. For instance, the measures described in our copending International patent application of even date (Attorney ref: 1620/1675/P/WO), claiming priority from United Kingdom patent application 0800459.0, may also be incorporated into the inhaler of the present invention.

The invention claimed is:

1. A dry powder inhaler comprising at least one medicament reservoir with an opening and a closure member engaged with the reservoir so as to close the opening, the reservoir having a first surface adjacent the opening and the closure member having an underside including a second surface, the first and second surfaces being in abutment via a deformable seal member interposed between the first surface and the closure member, the underside of the closure member including a pair of slots provided therein and the seal member being provided on the underside of the closure member and extending across substantially all of the underside of the closure member and into the pair of slots, wherein at least one of the first and second surfaces is formed with a projection that increases the contact pressure between the first and second surfaces as the projection engages the seal member, thereby improving a seal formed between the first and second surfaces and reducing the potential for ingress of moisture between the first and second surfaces into the reservoir.

2. A dry powder inhaler as claimed in claim 1, wherein the seal member is formed integrally with the closure member in a two-shot moulding process.

3. A dry powder inhaler as claimed in claim 1, wherein the material of the seal member is an elastomer.

4. A dry powder inhaler as claimed in claim 3, wherein the elastomer is a thermoplastic elastomer.

5. A dry powder inhaler as claimed in claim 4, wherein the thermoplastic elastomer is a thermoplastic polyester elastomer.

6. A dry powder inhaler as claimed in claim 1, wherein the projection extends around the full circumference of the opening in the reservoir.

7. A dry powder inhaler as claimed in claim 1, wherein the projection has a pointed profile.

8. A dry powder inhaler as claimed in claim 7, wherein the projection has a substantially triangular profile.

9. A dry powder inhaler as claimed in claim 1, wherein the projection is provided at the periphery of the opening in the reservoir.

10. A dry powder inhaler as claimed in claim 1, wherein the closure member is a cap, and the cap and the reservoir are provided with cooperating formations that engage to bring about sealing engagement of the cap with the reservoir.

11. A dry powder inhaler as claimed in claim 1, which comprises a metering member that closes an opening in the reservoir and which is adapted to transfer a unit dose of medicament from the reservoir to a position from which the dose of medicament can be inhaled by a user of the inhaler.

12. A dry powder inhaler as claimed in claim 11, wherein the metering member is rotatable and is formed with a series of cups that are sized such that each one of the series of cups can hold the dose of the medicament, such that rotation of the metering member moves one of the series of cups from a first position in which the one of the series of cups fills with medicament, to a second position external to the reservoir, at which the one of the series of cups is positioned adjacent to a path of an airflow through the inhaler whereby the dose of the medicament can be entrained in the airflow and inhaled.

13. A dry powder inhaler as claimed in claim 11, wherein the metering member is rotatable and takes the form of a frustoconical member that is urged into close engagement with a lower part of the reservoir.

14. A dry powder inhaler as claimed in claim 11, wherein the metering member moves in a linear or reciprocating manner.

* * * * *